United States Patent [19]
Leach

[11] Patent Number: 5,204,632

[45] Date of Patent: Apr. 20, 1993

[54] APPARATUS AND METHOD FOR DETECTING LEAKS IN SURGICAL AND EXAMINATION GLOVES

[76] Inventor: Eddie D. Leach, 627 Charlie Hicks Rd., Jonesborough, Tenn. 37659

[21] Appl. No.: 851,638

[22] Filed: Mar. 16, 1992

Related U.S. Application Data

[63] Continuation-in-part of Ser. No. 729,025, Jul. 12, 1991, abandoned, which is a continuation of Ser. No. 376,065, Jul. 5, 1989, abandoned.

[51] Int. Cl.⁵ .............................................. G01R 31/12
[52] U.S. Cl. ...................................... 324/557; 324/559
[58] Field of Search .................. 324/551, 554, 557–559

[56] References Cited

U.S. PATENT DOCUMENTS

| | | | |
|---|---|---|---|
| 2,981,886 | 4/1961 | Beck | 324/557 |
| 3,252,155 | 5/1966 | Surtees et al. | 340/242 |
| 3,721,970 | 3/1973 | Niemoth | 340/242 |
| 4,029,889 | 6/1977 | Mizuochi | 174/11 R |
| 4,112,417 | 9/1978 | Himeno | 340/605 |
| 4,558,273 | 12/1985 | Nishimura | 324/558 |
| 4,580,188 | 4/1986 | Brown et al. | 361/212 |
| 4,771,246 | 9/1988 | Boryta et al. | 324/559 |
| 4,776,209 | 10/1988 | Patchel | 73/45.5 |
| 4,799,384 | 1/1989 | Casali | 73/45.5 |
| 4,909,069 | 3/1990 | Albin et al. | 73/40 |

FOREIGN PATENT DOCUMENTS

| | | |
|---|---|---|
| 919775 | 1/1973 | Canada . |
| 942873 | 2/1974 | Canada . |
| 983579 | 2/1976 | Canada . |
| 1028392 | 3/1978 | Canada . |
| 1094157 | 1/1981 | Canada . |
| 1191202 | 7/1985 | Canada . |
| 1199969 | 1/1986 | Canada . |
| 859579 | 1/1961 | United Kingdom ............ 324/557 |

OTHER PUBLICATIONS

Proofs, Apr. 1989, p. 17, Penwell Publishing Company, 1421 S. Sheridan, Tulsa, Okla. 74112.
Judy Jakush, "Government Getting Ready to Test Gloves", ADA News, Apr. 3, 1989, pp. 22–23.
Holstein, Howard M., "Designing Quality In", Medical Device & Diagnostic Industry, pp. 32, 34–35, Oct. 1988.
Gobetti, John P.; Cerminaro, Michael and Shipman, Charles Jr., "Hand Asepsis: The Efficacy of Different Soaps in the Removal of Bacteria from Sterile, Gloved Hands", JADA, vol. 113, Aug. 1986, pp. 291–292.
Klein, Robert C.; Party, Esmeralda and Gershey, Edward L., "Virus Penetration of Examination Gloves", BioTechniques, vol. 9, No. 2, (1990) pp. 196–199.
Leters to the Editor, ADA, Oct. 1, 1990, 1 page.
Letters to the Editor, JADA, vol. 114, Jan. 1987, pp. 14 and 16.
Walter, Carl W., and Kundsin, Ruth B., "The Bacteriologic Study of Surgical Gloves from 250 Operations", Surg. Gynecol. Abstract 128: Nov. 1969, pp. 949–952.

*Primary Examiner*—Jack B. Harvey
*Attorney, Agent, or Firm*—Luedeka, Hodges, Neely & Graham

[57] ABSTRACT

An apparatus and method for detecting leaks in rubber or plastic articles such as surgical or examination gloves that, in general, are insulators against an electric current. The apparatus comprises a power source, first and second electrical leads, and structure for measuring the electrical properties between the leads. In the method of the invention the apparatus, together with an ion-containing liquid, complete an electrical circuit between the inside and the outside of the article when a hole in the article permits ions in the liquid to carry electrons through the hole. When used to test for holes in surgical or examination gloves during the use thereof or between such us as in the case of examination gloves, the test can be conveniently carried out while the practitioner washes or rinses his gloved hands under a non-recirculated stream of running tap water or flowing sterile saline solution.

12 Claims, 2 Drawing Sheets

APPARATUS AND METHOD FOR DETECTING LEAKS IN SURGICAL AND EXAMINATION GLOVES

This is a continuation-in-part of application Ser. No. 07/729,025, filed Jul. 12, 1991, which is a continuation of application Ser. No. 07/376,065, filed Jul. 5, 1989, both now abandoned.

BACKGROUND OF THE INVENTION

The present invention relates generally to the detection of leaks or faults in materials having electrical insulating properties, such as rubber or plastic surgical or examination gloves. More particularly the present invention is directed to apparatus and method for determining leaks in such a glove by establishing an electrical circuit through a leak in a glove due to the passage of ions through the leak by contacting the outer surface of the glove with a stream of ion-containing non-recirculated tap water or sterile saline solution.

Around the turn of the century, due in a large extent to work with bacteria began by Louis Pasteur, it became recognized that there is a need for protection against cross-contamination between patients and health care professionals, and subsequently between patients contacted by the health care professional. Because of this problem, many modern techniques have been developed to ensure disinfection and sterilization of instruments and equipment. Also to this end, barriers to microbes, such as gowns, face masks, and surgical or examination gloves are generally worn by the health care professional when potentially infectious conditions are encountered. More recently because of the spread of AIDS and hepatitis, health care professionals wear such barriers much more routinely than they did in the past.

Surgical or examination gloves do much to protect the health care professional from infection but are inconvenient and expensive if the gloves have to be changed between each patient. Fortunately, studies have shown that wearing rubber or plastic surgical or examination gloves, and washing the gloved hands between patients, is more effective in preventing cross-contamination between patients than is washing the hands, apparently because pores, wrinkles and the otherwise rough surface of the hands may sometimes protect trapped bacteria and viral agents from being washed away.

Because of the problems encountered in mass manufacturing and surgical or examination gloves, there is always a risk that a new glove might have a leak or undetectable micro-tear. Presently, federal regulations permit 4 out of every 100 examination gloves to have pinholes. The use, washing, and reuse of gloves tends to raise the probability that a leak or tear may develop. If a non-obvious leak or tear is present in a surgical or examination glove, the health care professional may be at risk without realizing the risk.

The leak testing of surgical gloves has been previously achieved by establishing electrical circuits through leaks in the gloves. In the use of such previous leak-testing techniques, electrical leads are directly or indirectly provided at the inner and outer surfaces of a glove to be leak tested and then the glove is immersed in a pool of ion-containing liquid such as a saline solution contained in a basin or contacted by a similar solution recirculated through the leak testing system. If a leak larger than the ions in the liquid is present in the glove, an electrical circuit is established through the leak to show that the glove is defective.

While these previous leak testing techniques may be satisfactory for leak testing surgical gloves before they are used, a significant problem arises when the gloves are checked for leaks during use or when gloves that are to be repeatedly used for medical procedures are leak tested between patients. This problem is due to the potential cross-contamination of gloves that are leak tested subsequent to the leak testing of a glove that is contaminated with one or more infectious organism since any infectious organism that have been "washed" from a tested glove supporting such organisms will be retained in the leak testing liquid contained in the basin or recirculated through the leak testing system so as to contaminate any glove that is subsequently tested for leaks.

The use of antibacterial agents in the leak testing liquid contained in the basin or recirculated through the system may possibly control some or many of the infectious organisms. However, there still remained a substantial possibility that if all the infectious organisms supported on the glove were not be controlled by the antibacterial agent the liquid in the basin or in the recirculating system would become contaminated. Also, such contamination of the liquid could also spread from the liquid to the basin or the components in the liquid recirculating system so as to create an undesirable source of contamination.

SUMMARY OF THE INVENTION

An object of the present invention to reduce or substantially eliminate the risk that a health care professional will become contaminated from an infectious patient while using a surgical or examination glove that has a small leak, tear or pinhole which is not readily apparent.

Another object of the present invention is to provide an apparatus and method for electrically determining the presence of leaks in surgical or examination gloves during the use thereof or between the use of such gloves that obviates or significantly reduces possible contamination problems encountered during the use thereof in the examination of a patient. This apparatus and method provides for the leak testing of such gloves by establishing an electrical circuit through a leak in the gloves by contacting a surface of the glove with ion-containing tap water or a saline solution running or flowing in a non-recirculated manner from an open faucet and a suitable container, respectively.

A further object of the present invention is to dispose of the water or saline solution through a drain coupled to a sewer or other suitable disposal site after a single use thereof so as to prevent cross contamination as might occur if several gloves are leak-tested in a reusable solution contained in a basin or recirculated through a leak checking system.

One aspect of the present invention is an apparatus for detecting leaks in a rubber or plastic article having an inside and an outside surface. The apparatus is used in conjunction with a flowing or running fluid, ion-containing liquid for contacting one surface of the article thereof. The apparatus comprises a first electrically conductive lead connected directly or indirectly to the flowing or running liquid and to one end of a power source; a second electrically conductive lead connected to the other end of the power source and adapted to contact a conductive element that may be placed in contact with the other surface of the article; and means for measuring the electrical properties between the first and second leads when a hole in the article permits completion of an electrical circuit when the ions in a stream of the liquid carry an electrical charge through the hole. The liquid is non-recirculated flowing or running tap water or saline solution having ions therein, and the article is a rubber or plastic surgical or examination glove.

A method is also provided for detecting a hole in such a rubber or plastic article having an inside and an outside surface which comprises the steps or placing the article on a conductive element that substantially fills said article to provide an article covered conductive element; connecting a first end of a first electrical lead to a power source and contacting a second end of a said first lead with a fluid containing ions; contacting the outside surface of the article covered conductive element with a flowing or running liquid containing ions; connecting a first end of a second electrical lead to the article covered conductive element and a second end of said second lead to a power source; and observing the electrical properties between the two electrical leads. In the present method, the article is defined by a surgical or examination glove, the conductive element is defined by the skin of a human hand and arm, and the ion-containing fluid is non-recirculated or single use tap water or saline solution, and the circuit, if a hole is present, is completed by touching the second lead to the skin of the arm above a gloved hand.

Other and further objects of the present invention will become obvious upon an understanding of the illustrative embodiments about to be described or will be indicated in the appended claims, and various advantages not referred to herein will occur to one skilled in the art upon employment of the invention in practice.

DETAILED DESCRIPTION OF THE INVENTION

The present invention is described in detail for its primary use in detecting leaks, tears and/or pinholes in surgical or examination gloves. It is to be understood, however, that the apparatus of the invention may easily be adapted to be used for the same purpose with many other articles having similar properties and uses.

Most surgical or examination gloves are made of some type of latex rubber or plastic which acts as a dielectric. That is, it will not allow the passage of ions which are driven by a given voltage unless there is a tear or perforation in the membrane making up the glove.

Ions are considerably smaller than the smallest of the known infectious agents, viruses. Bacteria are considerably larger than viruses. Therefore, if a glove is impervious to ions driven by an electric potential, then the glove should also be impervious to viruses and other infectious agents, which are many times larger than the ions, and are not driven by any electric potential. If ions can pass through a glove, then the glove should be judged defective and should be discarded, thus protecting both the patient and the health care professional.

Figure 1:
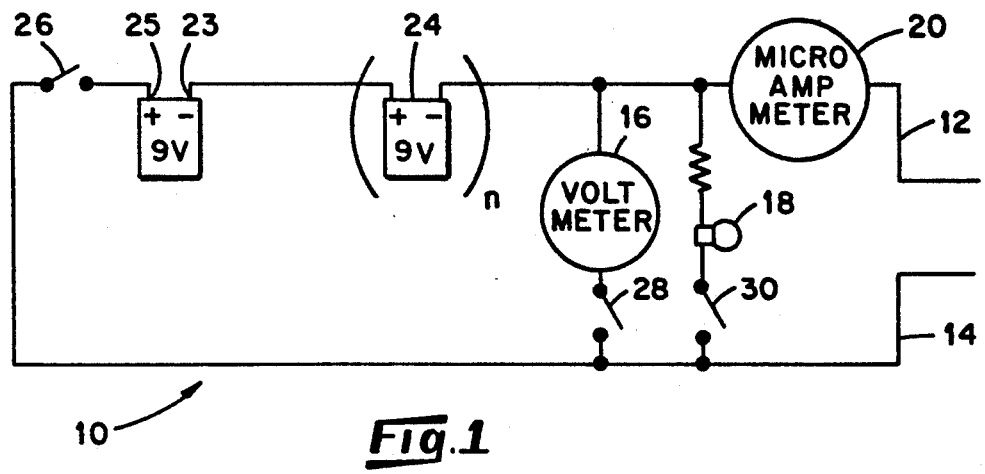
FIG. 1 is a schematic illustration of one embodiment the apparatus.

Referring now to FIG. 1, in a preferred embodiment, testing apparatus 10 of the invention comprises a first test lead 12 and a second test lead 14, test leads 12 and 14 being connected to opposite poles of battery power source 24. Battery power source 24 may comprise a number (n+1) of 9 volt batteries connected in series, where n can be 0 to 14. In the illustrated embodiment lead 12 is connected to negative pole 23, and lead 14 is connected to positive pole 25. It has been found that the particular polarity of the leads does not affect the test procedure. The power source is controlled by on/off switch 26. In the preferred embodiment the power source is rechargeable batteries. Volt meter 16, which is used to test the batteries, is in series with the batteries when switch 28 is closed. Test lamp 18, which is used to test the circuit, is in series with the batteries when switch 30 is closed. A test lamp is desirable because when a negative result is obtained using the apparatus, i.e., when an article such as a surgical or examination glove is tested that has no leaks, the circuit will not be completed to activate microampmeter 20, and some means is needed in the circuit to provide assurance to the operator that the circuits are operating correctly.

Microampmeter 20 will be in series with power source 24 when a leak develops in a glove or other article and a circuit is completed during testing.

Since, for proper operation, it is desirable that switches 28 and 30 be open when testing a surgical or examination glove, and switch 30 should be open when testing voltmeter 16, switches 28 and 30 may be provided as push button switches that are closed only as long as the operator maintains pressure on the switch.

It has been demonstrated that rubber or plastic examination gloves can be easily and effectively disinfected in a very short period of time, for example by washing the gloved hands with soap in running tap water before use. If this is done, and the glove checks to be safe through the use of the present invention, and the same procedures are followed before each use, than the same glove can be used in the treatment of several patients in a dental office, podiatrist, dermatologist, and other similar circumstances, where it is not practical to maintain operating room conditions.

Figure 2:
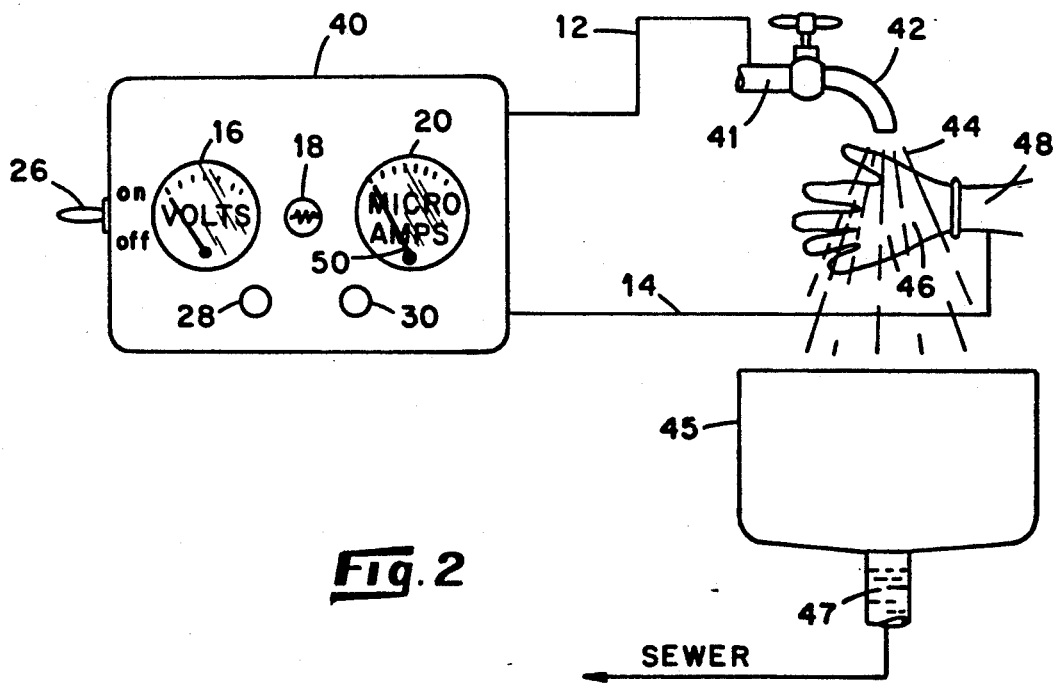
FIG. 2 is an illustration of the apparatus in use in one possible embodiment of the method of the invention.

With reference now to FIG. 2, an embodiment of the apparatus of the invention is illustrated in use in one possible method of using the invention. In the illustrated embodiment, the elements of the device are contained in cabinet 40. In the method, after testing the device to ensure that it is operating correctly, by first depressing switch 28 and then switch 30, test lead 12 is connected to a water pipe 41, or other electrical conductive portion of a faucet or tap 42, and the tap 42 is opened causing tap water 44 to flow from the tap 42 into a sink 45 having a drain 47 coupled to a suitable disposal such as a sewer or the like. The practitioner, while wearing surgical gloves, touches or has an assistant touch test lead 14 to his arm 48 above glove 46, and washes his hands with soap under the running water 44 which thereafter passes into the drain 47. If a leak, hole or tear is present in the glove, the ions in the tap water and/or in the soap used, carry a flow of electrons from power source 24 through water 44 to the hole or tear and into contact with the skin under the hole or tear. Since the skin conducts electricity, the skin and arm act as a conduit for carrying electrons to test lead 14 and back to power source 24. The flow of electrons through microampmeter 20 causes the needle 50 to react and measure the amount of current produced.

Since the human body is sensitive to electrical shock, it is desirable that the current, I=E/R, be kept very low. The resistance of skin to electrical current is in the megohm range, and accordingly, if the voltage of the power source is kept low, the current readings obtained will be in the microamp range, which produces an electron flow that is not detectable by most people. The high impedance, inherent resistance, and low amperage of the output circuitry help prevent detection, by electrical sock, of the low current flow.

It will be recognized by those skilled in the art that the amplitude of the reading obtained may be variable, subject to the size of the hole (more ions may breach the opening) and the position of the hole (the length of the skin patch needed to complete the circuit, and the type of skin traversed may cause some variation in the resistance). In general, however, it can be demonstrated that the apparatus is sensitive enough to detect an opening the size of a sodium ion, or larger. Any leak (or pore) smaller than a sodium ion is not big enough for any know bacteria or virus to breach.

If the voltage of power source is too small, the electromotive force (EMF) will not be great enough to drive the ions in the fluid to complete a circuit, and if the EMF is too high, the transfer of electrons through the glove may cause a hole in the glove where none existed before. Accordingly, the power source will provide about 5–90 volts, preferably 15–75 volts, and most preferably 20–50 volts. In the illustrated embodiment, the voltage provided is about 40 volts. A typical reading obtained on the microampmeter when a leak is detected in a glove when tested on a hand is about 25–50 microamps.

Instead of measuring current, those skilled in the art will recognize that a leak also may be detected by measuring the potential (voltage) between the test leads, or the resistance between the test leads.

Inasmuch as the water 44 from the tap 42 is used only once for washing and leak-testing the glove 46, any infectious organisms supported on the outer surface of the glove that were washed from the glove will be disposed of through the drain 47 so as to prevent the contamination of any subsequently tested glove. Also, while a tap with running water is illustrated in this embodiment for providing the leak-testing liquid, it will appear clear that this liquid could be readily provided by a sterile saline solution contained in a suitable vessel or container and provided with a suitable flow control such as a tap or the like for providing a flow of the saline water over the glove 46 and into the drain 47.

Figure 3:
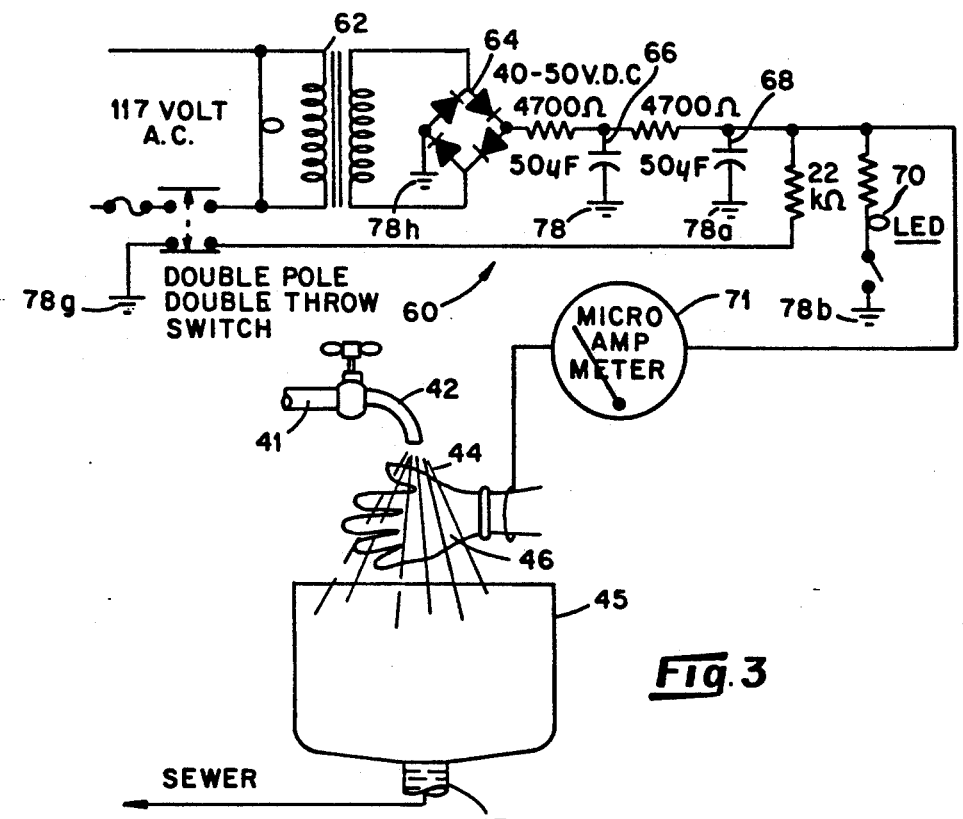
FIG. 3 is a schematic illustration of a second embodiment of the apparatus of the invention.

With reference now to FIG. 3, a schematic of an alternative embodiment of the apparatus 60 and a method is illustrated. The apparatus 60 is adapted to be connected to an A.C. (alternating current) power source, and since it is preferred that the current that contacts the skin be D.C. (direct current), apparatus 60 comprises (transformer) inductance coil 62, rectifier (filter circuit) 64, and capacitors 66 and 68 to convert A.C. to D.C. In the illustrated embodiment, a 120 volt primary to 24 volt secondary transformer is used to drive an A.C. to D.C. converter. Through proper filtering the pulsating D.C. is made into non-pulsating D.C. As illustrated, an LED 70 can be used to test the circuit and to provide a display means which lights to indicate the circuit is operating properly. A movement of the needle of the microampmeter 71 indicated when a leak, hole, of perforation is present in the article being tested.

As illustrated in FIG. 3, a water pipe 41 having a faucet or tap 42 is used to provide a stream of running water 44 which flows over the gloved hand of the practitioner and into a sink 45 having drain 47 coupled to a suitable disposal mechanism to carry out the test method. When using the embodiment of FIG. 3, the first test lead may be connected to a conductive portion of the water pipe 41 or tap 42 or to an electrode within the water pipe 41.

Yet another important feature of this embodiment would be single use of flowing sterile saline solution from a suitable container into the drain 47 in instances where maintaining sterile gloves and using aseptic techniques is required as in a hospital operating room setting or other similar circumstances. It has been found that about ¼ teaspoon of NaCl in 1 and ½ quarts of water provides a sufficient electrolyte solution for testing. Those skilled in the art will recognize that other electrolytes and other concentrations of electrolytes can be used.

Figure 4:
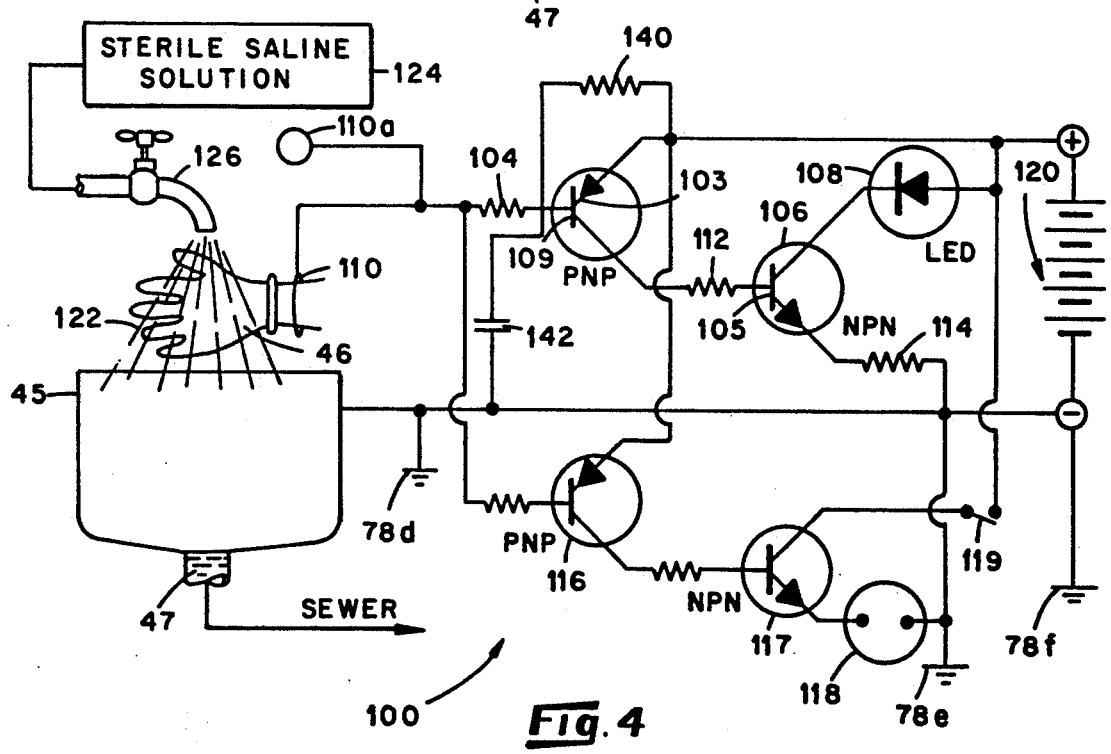
FIG. 4 is a schematic illustration of a third embodiment of the apparatus of the invention.

With reference now to FIG. 4, a third embodiment comprises a solid state apparatus in which the positive lead of LED 108 is connected to the positive battery terminal. The negative lead of the LED is connected to the collector of NPN transistor 106. The emitter of transistor 106 is connected to resistor 114 and the other end of resistor 114 is grounded at point 78. The NPN transistor 106 acts as a switch. When transistor 106 is switched on, the circuit is completed from the positive battery terminal through LED 108, on through transistor 106 and resistor 114 to ground so current can flow, and LED 108 will illuminate. Conversely, when transistor 106 is switched off, the circuit is opened, and current cannot flow through LED 108 on to ground and it is in an off or unlit condition.

As described above, the state of NPN transistor 106 is controlled by PNP transistor 102. The emitter 103 of transistor 102 is connected to the positive battery terminal and the collector is connected to the base of NPN transistor 106 through limiting resistor 112. Should transistor 102 be switched on, the emitter to collector voltage would decrease, raising the potential at the base 105 of transistor 106, which would cause it to switch on.

The state of the PNP transistor 102, (i.e., either on or off), is controlled by current flow through a voltage divider network made up of two resistances. The first resistance in the divider network is resistor 104 with one end connected to the base 109 of PNP transistor 102. The second resistance/impedance is a human hand in a latex glove 46. The hand is connected to resistor 104 via a metal ring 110. When a hole is in glove 46, the circuit is completed to ground by contacting the gloved hand with a stream 122 of sterile saline solution discharged from a suitable container or vessel 124 through a suitable faucet or tap 126. The stream 122 of saline solution after passing over the glove 46 enters sink 45 having a drain 47 coupled to a suitable disposal such as a sewer or the like.

Should a hole/puncture exist or develop in the latex glove 46, the ions in the liquid solution would be expected to penetrate the hole and make contact with the skin and thereby reduce the resistance of the network by several megohms. Because of the reduced resistance, current can flow from the positive battery terminal through the emitter base junction of PNP transistor 102, through resistor 104, to the skin, the solution and to ground. When this happens, transistor 102 is switched on, which switches transistor 106 on, and completes the circuit of LED 108 to ground, causing the LED to light. As soon as gloved hand is removed from the stream 122 of flowing saline solution, the total resistance of the divider network becomes very high, causing both transistors and the LED to switch to an off condition.

In the illustrated embodiment, resistor 104 has a resistance of 1 megohm, resistor 112 is 150 ohms, resistor 114 is, 150 ohms, resistor 140 is 0.5 megohm, and capacitor 142 is 0.002 microfarad. Those skilled in the art will recognize that a functional circuit can be constructed using other parameters.

In an alternative embodiment, a second wrist ring 110a may be provided, although, in general, a single electrode in contact with any part of the skin of the body, will cause a current flow which cause a current flow which will detect a hole in either glove.

The circuit can be tested by holding the wrist ring 110 in one hand (no glove) and grounding the other hand (no glove), on for example a metal tray. This will close the circuit and demonstrate that the remainder of the circuit is working properly by turning on the LED indicator light 108.

Because the embodiment of FIG. 4 uses a nine volt rechargeable battery 120 (relatively low voltage) there is no danger of shock to the person using the unit and no danger of damage to the gloves being tested.

An audible alarm circuit may be added by using PNP transistor 116 cascaded with transistor 117 as shown. In this case the load for transistor 117 is a low voltage buzzer. The divider network described above is used to bias transistor 116 on simultaneously with the other circuit so that a buzzer will sound at the same time that the LED illuminates. It should be recognized that the buzzer may be used to indicate a defective glove in addition to or in place of the LED.

Instead of using a stream of flowing saline solution for leak-testing gloves in the FIG. 4 embodiment, a stream of running water from a tap as in the FIGS. 2 and 3 embodiment may be utilized. Also, as pointed out in the description of the FIG. 1 embodiment, the single use of the water or saline solution in the embodiments of FIGS. 2, 3, and 4 will prevent the occurrence of cross-contamination problems.

The device of the present invention may be adapted to the operator, as opposed to connecting the wrist ring to the practitioner, for example, by providing the electrically conductive lead (corresponding to the wrist ring) permanently connected to the sink 45, but electrically insulated from the sink 45 (for example, standing beside the sink 45 like a car radio antenna), whereby the practitioner merely touches the conductive lead with bare skin while washing his hands. Other modifications will be apparent to those skilled in the art.

Those skilled in the art will recognize that such an apparatus can be used where the tested articles are made as quality control device. For example, in a factory where new gloves are leak-tested before any exposure to infectious microorganisms occurs, an electrically conductive hand prosthesis, when the article is a glove, can be placed in the glove, or the glove can be placed or formed over the hand prothesis, and the glove can then be immersed in a stream of electrolyte solution, and the test can be conducted otherwise as described above.

Those skilled in the art will recognize that the ion-containing fluid, in certain embodiments, especially for factory testing, may be an ion-containing gas.

Similarly, especially in a factory setting, instead of a hand, the conductive element which contacts one surface of the article also may be an ion-containing fluid.

While present embodiments of the invention and methods of practicing the same have been illustrated and described, it will be recognized by those skilled in the art that this invention may be otherwise variously embodied and practiced within the scope of the following claims.

What is claimed is:

1. An apparatus for detecting holes or perforations in a rubber or plastic surgical or examination glove having an inside surface and an outside surface with the latter being subject to contact with potentially infectious bacteria and viral agents during the use of said glove, said apparatus comprising:
   (a) liquid supply means for providing a non-recirculating stream of an ion-containing liquid;
   (b) a first electrically conductive lead having first and second ends with the first end indirectly contacting the outside surface of said glove through the stream of the ion-containing liquid when the outside surface of said glove is contacted by said stream of liquid and with the second end connected to a power source;
   (c) liquid receiving means for receiving and disposing of the stream of liquid after contact with the outside surface of said glove;
   (d) a second electrically conductive lead having a first end for directly contacting a conductive element which is adapted to substantially contact the inside surface of said glove and a second end attached to said power source; and
   (e) means for measuring the electrical properties between said first lead and said second lead when a leak through said glove allows ions in said liquid in contact with the outside surface of said glove to penetrate said leak and effect a completion of a circuit between said first lead and said second lead through said stream of liquid, said means for measuring being electrically connected with said first lead and said second lead.

2. An apparatus for detecting holes or perforations in a rubber or plastic surgical or examination glove as claimed in claim 1, wherein said liquid supply means provides a flow of tap water that defines said stream of ion-containing liquid, and wherein tap means are operatively associated with said liquid supply means for controlling the flow of said tap water therefrom.

3. An apparatus for detecting holes or perforations in a rubber or plastic surgical or examination glove as claimed in claim 2, wherein said liquid receiving means comprises sink means underlying said tap means and drain means coupled to said sink means for receiving said liquid and draining said liquid from said sink means.

4. An apparatus for detecting holes or perforations in a rubber or plastic surgical or examination glove as claimed in claim 3, wherein said liquid receiving means further comprises sewer means coupled to said drain means for receiving the liquid therefrom as sewage.

5. An apparatus for detecting holes or perforations in a rubber or plastic surgical or examination glove as claimed in claim 1, wherein said liquid supply means comprises container means for housing and providing a flow of sterile saline solution that defines said stream of ion-containing liquid, and wherein tap means are operatively associated with said container means for controlling the flow of said saline solution from said container means.

6. An apparatus for detecting holes or perforations in a rubber or plastic surgical or examination glove as claimed in claim 5, wherein said liquid receiving means comprises sink means underlying said tap means and drain means coupled to said sink means for receiving said liquid and draining said liquid from said sink means.

7. An apparatus for detecting holes or perforations in a rubber or plastic surgical or examination glove as claimed in claim 6, wherein said liquid receiving means further comprises sewer means coupled to said drain means for receiving the liquid therefrom as sewage.

8. A method for detecting a leak through a surgical or examination glove formed of a substantially non-conductive material and having an inside surface and an outside surface with the latter surface being subject to contact with potentially infectious bacteria and viral agents during the use of said glove, said method comprising the steps of:
  (a) placing said glove on a conductive element that substantially fills and contacts the inside surface of said glove to provide a glove-covered conductive element;
  (b) providing a stream of ion-containing liquid;
  (c) connecting a first end of a first electrical lead to the stream of ion-containing liquid and a second end of said electrical lead to an electrical power source;
  (d) immersing the outside surface of said glove in said stream of liquid for electrically coupling said first end of the first electrical lead to the outside surface of said glove;
  (e) connecting a first end of a second electrical lead to said conductive element and a second end of said lead to said power source;
  (f) observing the electrical properties between the first end of said first lead and the first end of said second lead using an electrical measuring device electrically connected to said first and second leads for the detecting of a leak through the glove during the contact of the outside surface thereof by the stream of liquid as determined by ions in said liquid penetrating said leak and completing an electrical circuit between said first and second leads; and
  (g) disposing without recirculating the stream of liquid after contact with the outside surface of said glove.

9. A method for detecting a leak through a surgical or examination glove formed of a substantially non-conductive material as claimed in claim 8, wherein the stream of ion-containing liquid is provided by a flow of tap water from an open tap.

10. A method for detecting a leak through a surgical or examination glove formed of a substantially non-conductive material as claimed in claim 9, wherein the step of disposing without recirculating the stream of liquid after contact with the outside surface of said glove is provided by conveying the tap water into drain means.

11. A method for detecting a leak through a surgical or examination glove formed of a substantially non-conductive material as claimed in claim 8, wherein the stream of ion-containing liquid is provided by a flow of sterile saline solution from a container having flow controlling tap means.

12. A method for detecting a leak through a surgical or examination glove formed of a substantially non-conductive material as claimed in claim 11, wherein the step of disposing without recirculating the liquid after contact with the outside surface of said glove is provided by conveying the saline solution into drain means.

* * * * *